(12) United States Patent
Appukuttan et al.

(10) Patent No.: US 11,319,414 B2
(45) Date of Patent: May 3, 2022

(54) SILICONE POLYMER

(71) Applicant: Momentive Performance Materials Inc., Waterford, NY (US)

(72) Inventors: Vinu Krishnan Appukuttan, Bangalore (IN); Pranabesh Dutta, Bangalore (IN); Sandeep Naik, Bangalore (IN); Anubhav Saxena, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 15/928,485

(22) Filed: Mar. 22, 2018

(65) Prior Publication Data
US 2019/0292322 A1 Sep. 26, 2019

(51) Int. Cl.
| C08G 77/38 | (2006.01) |
| C08G 77/392 | (2006.01) |
| C09K 5/14 | (2006.01) |
| A61K 8/899 | (2006.01) |
| A61K 8/891 | (2006.01) |
| A61Q 19/00 | (2006.01) |
| C08G 77/00 | (2006.01) |

(52) U.S. Cl.
CPC ............ C08G 77/392 (2013.01); A61K 8/891 (2013.01); A61K 8/899 (2013.01); A61Q 19/00 (2013.01); C08G 77/38 (2013.01); C09K 5/14 (2013.01); *A61K 2800/10* (2013.01); *C08G 77/70* (2013.01); *C08G 77/80* (2013.01)

(58) Field of Classification Search
CPC ............................. C08G 77/392; C08G 77/38
USPC ................................................ 528/27, 25, 30
See application file for complete search history.

(56) References Cited

U.S. PATENT DOCUMENTS

| 3,414,604 A * | 12/1968 | Pepe ........................ C10M 3/00 556/440 |
| 3,668,273 A | 6/1972 | Krantz |
| 4,226,761 A | 10/1980 | Cooper et al. |
| 4,725,658 A | 2/1988 | Thayer et al. |
| 4,774,028 A * | 9/1988 | Imai ........................ C08G 77/04 552/505 |
| 4,814,392 A | 3/1989 | Shea et al. |
| 5,034,490 A * | 7/1991 | Jacobine .............. C08G 75/045 528/30 |
| 5,204,438 A | 4/1993 | Snow et al. |
| 5,357,022 A | 10/1994 | Banach et al. |
| 5,380,527 A | 1/1995 | Legrow et al. |
| 5,412,055 A * | 5/1995 | Loo ........................... C07F 7/20 528/14 |
| 5,596,048 A | 1/1997 | Blohm et al. |
| 5,605,649 A * | 2/1997 | Stohrer ................ C09K 19/406 252/299.01 |
| 5,641,850 A * | 6/1997 | Stohrer ................. C07F 7/0879 528/15 |
| 5,656,197 A | 8/1997 | Hsiue et al. |
| 5,662,828 A * | 9/1997 | Tsubata .............. C09K 19/0225 252/299.01 |

(Continued)

FOREIGN PATENT DOCUMENTS

| CN | 102634212 | 8/2012 |
| CN | 103849356 | 6/2014 |

(Continued)

OTHER PUBLICATIONS

Patent Cooperation Treaty (PCT), International Search Report and Written Opinion for Application PCT/US2019/022262 filed Mar. 14, 2019, dated May 29, 2019, International Searching Authority, EP.

(Continued)

*Primary Examiner* — Margaret G Moore
(74) *Attorney, Agent, or Firm* — McDonald Hopkins LLC; Joseph Waters

(57) ABSTRACT

Provided is a silicone polymer of the Formula (I):

$$M^1_a M^2_b M^3_c D^1_d D^2_e D^3_f T^1_g T^2_h T^3_i Q_j.$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group; $R^4$, $R^{12}$, $R^{17}$ are independently chosen from a C1-C60 alkyl, a C1-C60 alkoxy, or $R^{19}$-A-$R^{20}$— where A is chosen from a group comprising an unsaturated cyclic moiety chosen from an aromatic group, a fused aromatic group, an unsaturated alicyclic group, an unsaturated heterocyclic group, or a combination of two or more thereof; $R^{19}$ is chosen from a —H, a C1-C60 alkyl, allyl, vinyl, alkoxy, allyloxy, vinyloxy, acrylate, or methacrylate; and $R^{20}$ is chosen from a divalent organic group;
$R^7$, $R^{14}$, $R^{18}$ are independently selected from hydrogen or $OR^{22}$ or unsaturated monovalent radicals or radicals containing heteroatom such as oxygen, nitrogen, sulfur or radicals containing organosilane groups; and
the subscripts a, b, c, d, e, f, g, h, i, j are zero or positive subject to the following limitations: 2≤a+b+c+d+e+f+g+h+i+j≤1000, b+e+h>0 and c+f+i≥0.

12 Claims, No Drawings

(56) References Cited

U.S. PATENT DOCUMENTS

| | | | |
|---|---|---|---|
| 5,916,952 | A | 6/1999 | Romenesko et al. |
| 6,300,454 | B1* | 10/2001 | Hanelt ............... G02F 1/133711 |
| | | | 528/27 |
| 6,358,574 | B1* | 3/2002 | Haberle ................. C08G 77/38 |
| | | | 106/481 |
| 6,492,030 | B1* | 12/2002 | Hashimoto .......... C08G 73/106 |
| | | | 428/447 |
| 6,783,692 | B2 | 8/2004 | Bhagwagar |
| 6,815,486 | B2 | 11/2004 | Bhagwagar et al. |
| 6,869,642 | B2 | 3/2005 | Freuler et al. |
| 7,074,490 | B2 | 7/2006 | Feng et al. |
| 7,109,288 | B2 | 9/2006 | Akatsuka et al. |
| 7,579,425 | B2 | 8/2009 | Terry et al. |
| 7,652,162 | B2* | 1/2010 | Silvi ................... C08G 77/392 |
| | | | 556/429 |
| 8,084,549 | B2* | 12/2011 | Silvi ................... C08G 77/392 |
| | | | 525/343 |
| 8,921,507 | B2 | 12/2014 | Yoshihara et al. |
| 9,209,104 | B2 | 12/2015 | Nguyen et al. |
| 2003/0096919 | A1 | 5/2003 | Ichinohe |
| 2005/0288468 | A1* | 12/2005 | Ohno ........................ C07F 7/21 |
| | | | 526/317.1 |
| 2007/0051773 | A1 | 3/2007 | Ruchert et al. |
| 2007/0149703 | A1 | 6/2007 | Caprasse et al. |
| 2007/0208144 | A1 | 9/2007 | Delsman et al. |
| 2008/0302064 | A1 | 12/2008 | Rauch |
| 2019/0144752 | A1 | 5/2019 | Hannington et al. |

FOREIGN PATENT DOCUMENTS

| | | |
|---|---|---|
| CN | 105018043 | 11/2015 |
| DE | 19857691 | 6/2000 |
| EP | 0163495 | 12/1985 |
| EP | 0291884 | 11/1988 |
| EP | 2562200 | 2/2013 |
| JP | 11323162 | 11/1999 |
| JP | 2007051221 | 3/2007 |
| JP | 2008214599 | 9/2008 |
| JP | 6125221 | 5/2017 |
| WO | 2017213809 | 12/2017 |

OTHER PUBLICATIONS

Shen et al., "Polyethylene nanofibers with very high thermal conductivities." Nature Nanotechnology, 2010, vol. 5 (4), pp. 251-255.
Singh et al., "High thermal conductivity of chain-oriented amorphous polythiophene." Nature Nanotechnology, 2014, vol. 9, pp. 384-390.

* cited by examiner

SILICONE POLYMER

FIELD

The present invention relates to a silicone polymer. In particular, the present invention relates to a functionalized siloxane polymer comprising unsaturated cyclic moieties that exhibits thermoplastic and elastomeric properties over a wide range of temperatures and demonstrates reversible phase change behavior with improved physical properties such as thermal conductivity.

BACKGROUND

Polydimethylsiloxane (PDMS) polymers are generally room temperature liquids owing to their microstructures and they are used primarily for its viscoelastic behavior. But such PDMS fluid find limited application where high mechanical properties are required, such as ability to display high thermal transitions (or melting points), impact toughness, dimensional stability, low permeability. In addition, the amorphous nature of PDMS render it low in thermal conductivity. One common method to improve the mechanical properties is by blending siloxane polymer with thermoplastic polymer or by using fillers. However, such techniques may have poor storage stability and phase separation issues. Other techniques used to make solid silicone is through silicone resins by incorporating tertiary (T) and quaternary (Q) silicone group or by cross-linking, but the technique will result in thermoset. Both method are generally marred by it challenges in post-processing and application methods. Soft thermoplastic silicones could be made through simple organic modification of silicones or through co-polymerization. U.S. Publication 2003/0096919, U.S. Pat. Nos. 4,725,658, 7,579,425 describe the incorporation long chain hydrocarbon in the form of fatty acid, 1-olefins to silicone chain to make soft thermoplastic silicones. CN 201410102937 and U.S. Publication 20080302064 depict the concept of phase change silicone composition which uses long chain aliphatic paraffinic waxes, silicone copolymer with aliphatic hydrocarbon, polyolefins.

Polymers are generally thermal insulators due to the amorphous arrangement of the molecular chains, which offer resistance to transport of heat-conducting phonons. Better heat conductivity may be obtained by improving the packing of the polymer or by introducing crystalline segments in the polymer. Attempts to improve thermal conductivity are described in Nature Nanotechnology 2010, 5(4), 251-55; Nature Nanotechnology 2014, 9, 384-90. U.S. Pat. No. 7,109,288; EP 2562200, and Japanese patent publication JP 11-323162, use the concept of incorporating mesogenic group in non-silicone resin to enhance thermal conductivity. Similar concept is used in Japanese patent 2007-051221 and 2008-214599 to make room temperature fluid curable mesogen-silicone resin. Such resin on curing give high T/C.

SUMMARY

The present invention relates to a functionalized siloxane polymers comprising unsaturated cyclic moieties.

In particular, functionalized siloxane polymers include grafting of arylene ethers in silicone polymers or resin to impart crystalline segments in the polymer matrix. The arylene ether groups may be placed pendant to the siloxane chain or at the terminal ends of the chain/matrix. The polymers may be curable or non-curable and may include a reactive/curable group terminal or pendant to the siloxane main chain.

In one aspect of the invention, functionalized siloxane polymers exhibit improved thermal conductivity.

In one aspect of the invention, the functionalized siloxane polymers have phase change characteristics and exhibit reversible thermoplastic elastomeric properties over a wide range of temperatures. The polymer may be a solid, fluid, gum, or waxy liquid under various conditions.

In one aspect of the invention, the properties of the functionalized siloxane polymers may be tuned by controlling aspects of the polymer including, for example, the molecular weight of the polymer, the ratio of the various siloxane units (i.e., the M, D, T, and Q units), the concentration of the arylene ether groups, etc.

In one aspect, provided is a silicone polymer of the Formula (I):

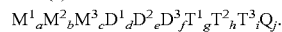

wherein:

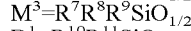
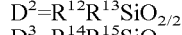
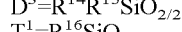
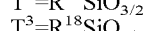
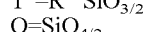
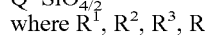

$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C60 alkyl, a C1-C60 alkoxy, or $R^{19}$-A-$R^{20}$— where A is chosen from a group comprising an unsaturated cyclic moiety chosen from an aromatic group, a functionalized aromatic group, a fused aromatic group optionally containing a heteroatom, an unsaturated alicyclic group, an unsaturated heterocyclic group, or a combination of two or more thereof; $R^{19}$ is chosen from a —H, a C1-C60 alkyl or allyl or aryl or vinyl, optionally containing heteroatom(s), acrylate, or methacrylate; and $R^{20}$ is chosen from a divalent organic group;

$R^7$, $R^{14}$, $R^{18}$ are independently selected from hydrogen or $OR^{22}$ or unsaturated monovalent radicals or radicals containing heteroatom such as oxygen, nitrogen, sulfur or radicals containing organosilane groups; and the subscripts a, b, c, d, e, f, g, h, i, j are zero or positive subject to the following limitations: $2 \leq a+b+c+d+e+f+g+h+i+j \leq 1000$, $b+e+h>0$ and $c+f+i \geq 0$.

In one embodiment, A is chosen from a group of the formula -$A^1$-$R^{21}$-$A^2$- where $A^1$ and $A^2$ are independently chosen from a C6 to C12 aryl group, C12-C36 fused aromatic ring group, a C5-C36 unsaturated alicyclic group, and a C5-C36 unsaturated heterocyclic group; and $R^{21}$ is chosen from a direct bond, —(CH$_2$)$_n$—, —C(CH$_3$)$_2$—, —O—, —S—, —S(O)$_2$—, —C(O)—, C(O)—NH—, —NH—C(O)—NH—, C(O)—O—, —CH=N—, or —CH=N—N=CH— where n is 1-10.

In one embodiment, A is independently chosen from

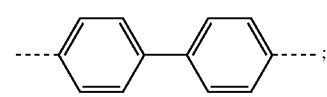

(A-i)

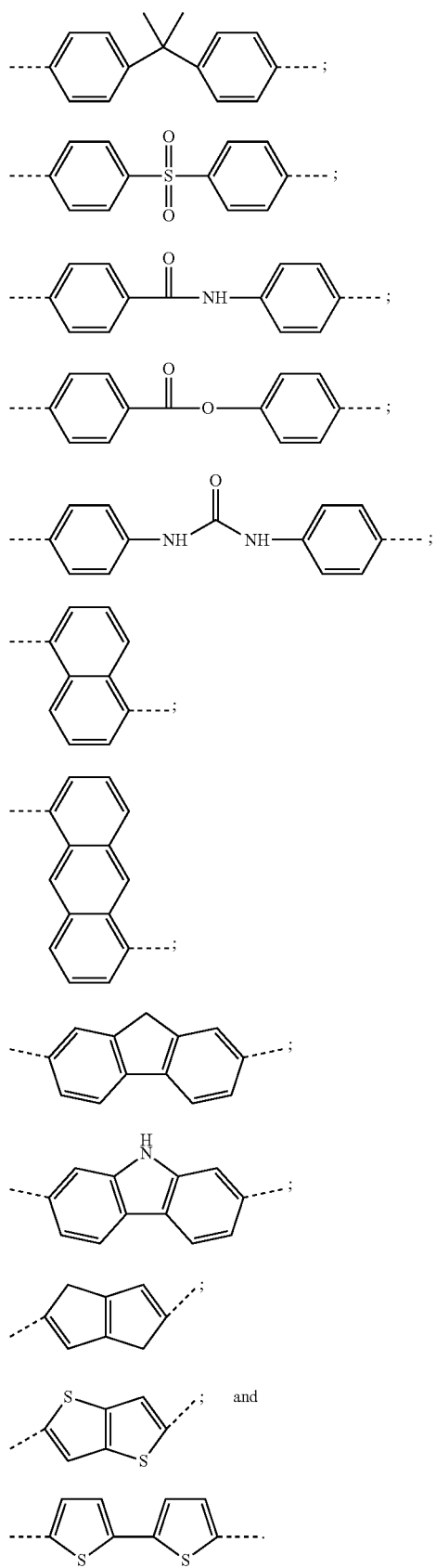

(A-ii)
(A-iii)
(A-iv)
(A-v)
(A-vi)
(A-vii)
(A-viii)
(A-ix)
(A-x)
(A-xi)
(A-xii)
(A-xiii)

In one embodiment, A in $R^4$, $R^{12}$ and $R^{17}$ is

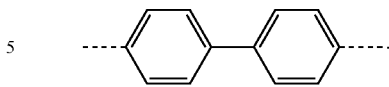

In one embodiment, A in $R^4$, $R^{12}$ and $R^{17}$ is

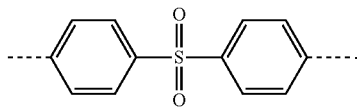

In one embodiment of the polymer of any previous embodiment, $R^{19}$ is chosen from —H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$—, or —O—C(O)—$(CH2)_m$—, and m is 2-10.

In one embodiment of the polymer of any previous embodiment, $R^1$, $R^2$, $R^3$, $R^5$, $R^6$, $R^8$, $R^9$, $R^{10}$, $R^{11}$, $R^{15}$, $R^{16}$ are methyl.

In one embodiment of the polymer of any previous embodiment, the unsaturated monovalent radical in the present invention can be selected from the group of the formulae (I) to (V):

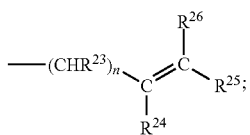 (I)

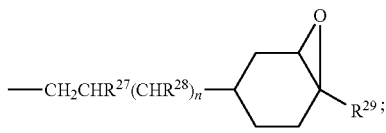 (II)

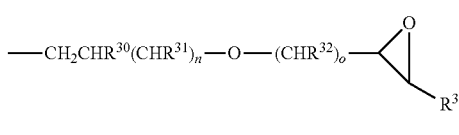 (III)

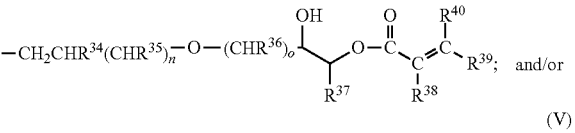 (IV)

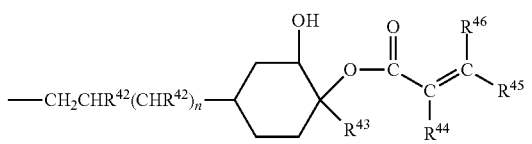 (V)

wherein $R^{23}$, $R^{28}$, $R^{31}$, $R^{32}$, $R^{35}$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, $R^{39}$, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6.

In one embodiment of the polymer of any previous embodiment, the polymer has peak melting temperature of more than 20° C.

In one embodiment of the polymer of any previous embodiment, the polymer has peak melting temperature is from 23° C. to 100° C.

In one embodiment of the polymer of any previous embodiment, the polymer has a number average molecular weight of from about 100 g/mol to about 12000 g/mol.

In one embodiment of the polymer of any previous embodiment, the polymer has a thermal conductivity in the range of 0.1 to 0.5 W/m·K.

In another aspect, provided is a product comprising the polymer of any previous embodiment.

In one embodiment, the product is chosen from an automotive product, household product, paint, coating, laundry detergent, textile treatment, oil or gas product, fuel cell, electronic product, agriculture product, aerospace product, medical or health care product, membrane, construction product, adhesive, sealant, injection moldable and compression moldable rubber or plastic, or silicone based rubber.

In one embodiment, the product is chosen from light emitting devices, computer devices, a stacked die, mobile phones, tablets, flip chip package, hybrid memory cube, touch screens, Wi-Fi device, automotive technology hifi systems, a through-silicon via device, and audio systems, in joints between heat pipes and water tanks in solar heated heating, in fuel cells and wind turbines, in the manufacture of computer chips, gaming consoles, data transfer devices, in light devices, batteries, in housings, coolers, heat exchanging devices, wires, cables, heating wires, refrigerators, dishwashers, air conditionings, accumulators, transformers, lasers, functional clothing, car seats, medical devices, fire protection, electric motors, planes, and trains, as a filament for 3D printing material, drug delivery systems, transdermal patches, wound healing patches, wound dressing patches, patches for scar reduction, transdermal iontophoresis, scaffold for tissue engineering, anti-microbial devices, wound management devices, ophthalmic devices, bioinserts, prostheses, body implants, paints, structural coating, masonry coating, or marine coating, seed coating, superspreader or controlled release fertilizer.

In yet another aspect, provided is a personal care product comprising the polymer of any previous embodiment.

In one embodiment, the personal care product is in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a cucumber slices, a skin pads, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouth-wash, a massage oil, a toothpaste, a clear gel or stick, an ointment base, a topical wound-healing product, an aerosol talc, a barrier spray, a vitamin and anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

DETAILED DESCRIPTION

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" mean an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Provided is a functionalized silicone polymer In particular, provided is a functionalized siloxane polymer. The siloxane polymer comprises organic groups comprising unsaturated cyclic moieties. The present siloxane polymers have been found to exhibit good thermal stability and thermal conductivity.

Provided is a silicone polymer of Formula (I)

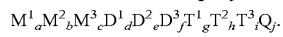
$M^1{}_aM^2{}_bM^3{}_cD^1{}_dD^2{}_eD^3{}_fT^1{}_gT^2{}_hT^3{}_iQ_j$.

wherein:
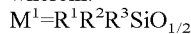
$M^1=R^1R^2R^3SiO_{1/2}$
$M^2=R^4R^5R^6SiO_{1/2}$
$M^3=R^7R^8R^9SiO_{1/2}$
$D^1=R^{10}R^{11}SiO_{2/2}$
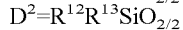
$D^2=R^{12}R^{13}SiO_{2/2}$
$D^3=R^{14}R^{15}SiO_{2/2}$
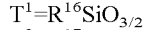
$T^1=R^{16}SiO_{3/2}$
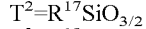
$T^2=R^{17}SiO_{3/2}$
$T^3=R^{18}SiO_{3/2}$
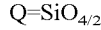
$Q=SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C60 alkyl, a C1-C60 alkoxy, or $R^{19}$-A-$R^{20}$— where A is chosen from a group comprising an unsaturated cyclic moiety chosen from an aromatic group, a fused aromatic group, an unsaturated alicyclic group, an unsaturated heterocyclic group, or a combination of two or more thereof; $R^{19}$ is chosen from a —H, a C1-C60 alkyl, allyl, vinyl, alkoxy, allyloxy, vinyloxy, acrylate, or methacrylate; and $R^{20}$ is chosen from a divalent organic group;

$R^7$, $R^{14}$, $R^{18}$ are independently selected from hydrogen, $OR^{22}$, an unsaturated monovalent radical, a radical containing a heteroatom such as oxygen, nitrogen, sulfur, or a radical containing organosilane groups; and the subscripts a, b, c, d, e, f, g, h, i, and j are zero or positive subject to the proviso that 2≤a+b+c+d+e+f+g+h+i+j≤1000, b+e+h>0, and c+f+i≥0.

As used herein, an unsaturated alicyclic group refers to an aliphatic cyclic group comprising one or more unsaturated bonds. In embodiments, the unsaturated alicyclic group comprises at least one C=C bond. In embodiments, the unsaturated alicyclic group is chosen from a C4-C36 alicyclic group comprising one or more C=C bonds. The unsaturated alicyclic group may comprise a single ring, a fused ring system, or a bicyclic ring system. Non-limiting examples of unsaturated alicyclic compounds include, but are not limited to, cyclopentene, cyclohexene, cyclopentadiene, dicyclopentadiene, etc.

As used herein, an unsaturated heterocyclic group refers to a cyclic group comprising at least one unsaturated bond and at least one heteroatom within the ring structure. The unsaturated group may be a C=C or an unsaturated bond between a carbon atom and a heteroatom.

In embodiments, $R^{19}$ is chosen from —H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$—, or —O—C(O)—$(CH2)_m$—, and m is 2-10. In one embodiment, $R^{19}$ is $CH_2$=$CH_2$—$(CH_2)_l$—O— where l is 0. In one embodiment, $R^{19}$ is $CH_2$=$CH_2$—$(CH_2)_l$—O— where l is 1.

In embodiments, A is independently chosen from a C6 to C12 aryl group, a C12 to C36 fused aromatic group, a C4-C36 unsaturated alicyclic group, and a C4-C36 unsaturated heterocyclic group.

In on embodiment, A is chosen from a group of the formula -$A^1$-$R^{21}$-$A^2$- where $A^1$ and $A^2$ are independently chosen from a C6 to C12 aryl group, a C12-C36 fused aromatic ring, a C5-C36 unsaturated alicyclic group, and a C5-C36 unsaturated heterocyclic group; and $R^{21}$ is chosen from a direct bond —$(CH_2)_n$—, —$C(CH_3)_2$—, —O—, —S—, —$S(O)_2$—, —C(O)—, C(O)—NH—, —NH—C(O)—NH—, C(O)—O—, —CH=N—, or —CH=N—N=CH— where n is 1-10. In embodiments, n is 1-6, 1-4, or 1-2.

Examples of suitable groups for the A groups include, but are not limited to:

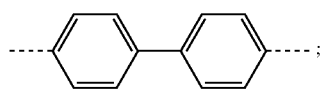
(A-i)

(A-ii)

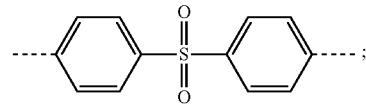
(A-iii)

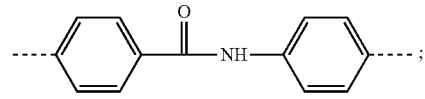
(A-iv)

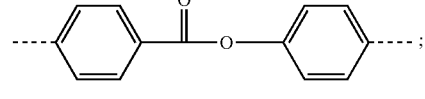
(A-v)

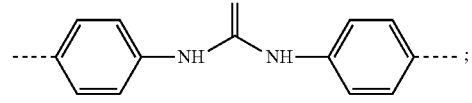
(A-vi)

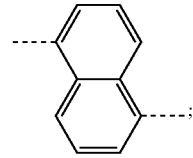
(A-vii)

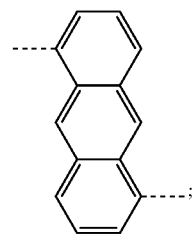
(A-viii)

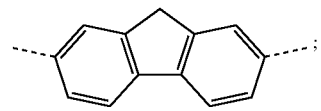
(A-ix)

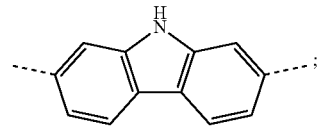
(A-x)

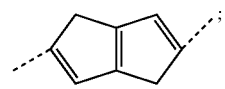
(A-xi)

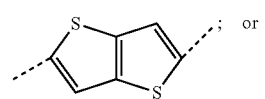
; or
(A-xii)

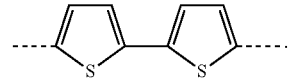
(A-xiii)

In one embodiment, $R^1$, $R^2$, $R^3$, $R^5$, $R^6$, $R^8$, $R^9$, $R^{10}$, $R^{11}$, $R^{13}$, $R^{15}$, $R^{16}$ are a C1-C4 alkyl, A is

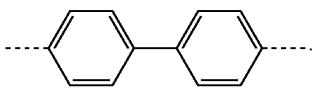

$R^{19}$ is chosen from —H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$—, or —O—C(O)—$(CH2)_m$—, and m is 2-10. In one embodiment, $R^{19}$ is $CH_2$=$CH_2$—$(CH_2)_l$—O— where l is 0. In one embodiment, $R^{19}$ is $CH_2$=$CH_2$—$(CH_2)_l$—O— where l is 1.

In one embodiment, $R^1$, $R^2$, $R^3$, $R^5$, $R^6$, $R^8$, $R^9$, $R^{10}$, $R^{11}$, $R^{13}$, $R^{15}$, $R^{16}$ are a C1-C4 alkyl, A is

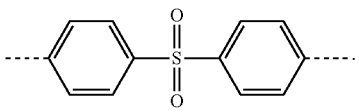

$R^{19}$ is chosen from —H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$—, or —O—C(O)—$(CH2)_m$—, and m is 2-10. In one embodiment, $R^{19}$ is $CH_2$=$CH_2$—$(CH_2)_l$—O— where l is 0. In one embodiment, $R^{19}$ is $CH_2$=$CH_2$—$(CH_2)_l$—O— where l is 1.

In one embodiment, A is chosen from any one of (A-i)-(A-xiii), and $R^{19}$—H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$—, or —O—C(O)—$(CH2)_m$—, and m is 2-10. In one embodiment A is chosen from any of (A-i)-(A-xiii); $R^{19}$ is chosen from $CH_2$=$CH_2$—$(CH_2)_l$—O— where l is 0 and $R^{20}$ is chosen from —O—$(CH_2)_m$— where m is 2. In one embodiment A is chosen from any of (A-i)-(A-xiii); $R^{19}$ is chosen from $CH_2$=$CH_2$—$(CH_2)_l$—O— where l is 0 and $R^{20}$ is chosen from —O—$(CH_2)_m$— where m is 3. In one embodiment A is chosen from any of (A-i)-(A-xiii); $R^{19}$ is chosen from $CH_2$=$CH_2$—$(CH_2)_l$—O— where l is 1 and $R^{20}$ is chosen from —O—$(CH_2)_m$— where m is 2. In one embodiment A is chosen from any of (A-i)-(A-xiii); $R^{19}$ is chosen from $CH_2$=$CH_2$—$(CH_2)_l$—O— where l is 1 and $R^{20}$ is chosen from —O—$(CH_2)_m$— where m is 3.

In one embodiment, the A containing group is pendant to the siloxane chain.

In embodiments, $R^7$, $R^{14}$, $R^{18}$ are chosen from an unsaturated monovalent radical can be chosen from the group of the formulae (I) to (V)

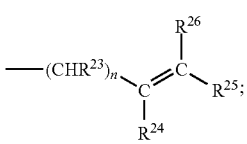
(I)

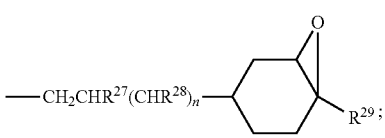
(II)

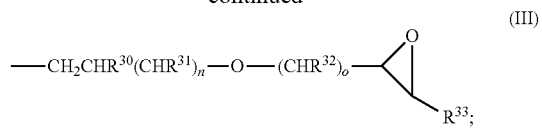
(III)

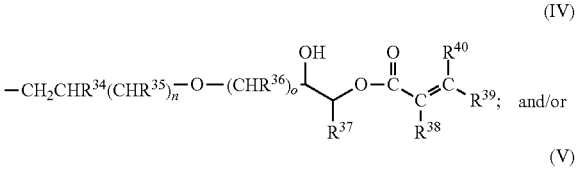
(IV)

and/or

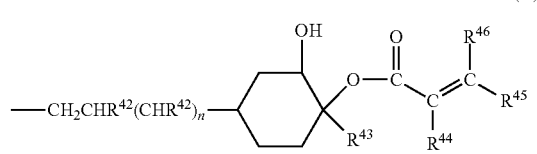
(V)

wherein $R^{23}$, $R^{28}$, $R^{31}$, $R^{32}$, $R^{35}$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, $R^{39}$, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6

The present polymers may be formed via hydrosilylation of an appropriate unsaturated compound and a silyl hydride in the presence of a catalyst. The unsaturated compounds to provide the $R^4$, $R^{12}$, $R^{17}$ groups may be of the formula $R^{19}$-A-$R^{19'}$ where A is as described above, and $R^{19}$ and $R^{19'}$ are independently chosen from allyl, vinyl, allyloxy, vinyloxy, acrylate, or methacrylate. In embodiments, $R^{19}$ and $R^{19'}$ are independently chosen from $CH_2$=$CH_2$—$(CH_2)_a$—, $CH_2$=$CH_2$—$(CH_2)_a$—O—, $CH_2$=$CH_2$—$(CH_2)_a$—C(O)—O—, where a is 0-10. The silyl hydride may be, for example, a siloxane with terminal silyl hydride functional groups or with a Si—H containing group within the main chain of the siloxane or with Si—H containing group within silicone resin with T or Q structure.

Useful catalysts to form the polymer include those compounds or molecules that can catalyze the hydrosilylation reaction between a reactive SiH-containing moiety or substituent and a carbon-carbon bond such as a carbon-carbon double bond. Also, in one or more embodiments, these catalysts may be soluble within the reaction medium. Types of catalysts include transition metal compounds including those compounds that include a Group VIII metal. Exemplary Group VIII metals include palladium, rhodium, germanium, and platinum. Exemplary catalyst compounds include chloroplatinic acid, elemental platinum, chloroplatinic acid hexahydrate, complexes of chloroplatinic acid with sym-divinyltetramethyldisiloxane, dichloro-bis(triphenylphosphine) platinum (II), cis-dichloro-bis(acetonitrile) platinum (II), dicarbonyldichloroplatinum (II), platinum chloride, and platinum oxide, zero valent platinum metal complexes such as Karstedt's catalyst, [Cp*Ru(MeCN)$_3$] PF$_6$, [PtCl$_2$(cyclooctadiene)], solid platinum supported on a carrier (such as alumina, silica or carbon black), platinum-vinylsiloxane complexes (e.g., Pt$_n$(ViMe$_2$SiOSiMe$_2$Vi)$_c$ and Pt[(MeViSiO)$_4$]$_d$)), platinum-phosphine complexes (e.g., Pt(PPh$_3$)$_4$ and Pt(PBU$_3$)$_4$)), and platinum-phosphite complexes (e.g., Pt[P(Oph)$_3$]$_4$ and Pt[P(Obu)$_3$]$_4$)), wherein Me represents methyl, Bu represents butyl, "Vi" represents vinyl and Ph represents phenyl, and c and d represent integers. Others include $RhCl(PPh_3)_3$, $RhCl_3$, $Rh/Al_2O_3$, $RuCl_3$, $IrCl_3$, $FeCl_3$, $AlCl_3$, $PdCl_2.2H_2O$, $NiCl_2$, $TiCl_4$, etc.

The properties or state of the polymer can be controlled or tuned by controlling various aspects of the polymer. In particular, the polymer may be provided as a liquid, a gum, or a solid by controlling the degree of polymerization, silicone chain length, and molecular weight.

In one embodiment, the silicone polymer has a number average molecular weight of from about 100 g/mol to about 100000 g/mol; from about 500 g/mol to about 50000 g/mol; even from about 600 g/mol to about 12000 g/mol. Molecular weight may be determined by Gel Permeation Chromatography.

The polymers exhibit properties that make them useful in a variety of applications. The polymers may exhibit reversible thermoplastic behavior. The polymers possess both plastic and elastomeric properties over a wide range of temperatures. The phase change temperature of the polymers is from about 10° C. to about 120° C. The properties or state of the polymer can be controlled or tuned by controlling various aspects of the polymer. In particular, the polymer may be provided as a liquid, a gum, or a solid by controlling the degree of polymerization, silicone chain length, and molecular weight. The properties, e.g., melting/phase change behavior, may be tuned or selected by the silicone segment (e.g., size or number of m and x units) and the divalent unsaturated cyclic groups A).

The present polymers have been found to exhibit desirable properties that may make them suitable for a wide variety of applications. The polymers have high thermal stability, refractive index, and thermal conductivity.

In embodiments, the copolymer of the present invention may also find use as a thixotropic agent or a rheology modifying agent. A "thixotropic agent" as used herein is one that increases the thixotropy of the composition in which it is contained, promoting shear thinning and enabling use of reduced injection force.

The present polymers have been found to exhibit desirable properties that may make them suitable for a wide variety of applications. The polymers have high thermal stability, refractive index, and thermal conductivity. The have excellent wetting behavior when combined with inorganic fillers such that the fillers are readily dispersed in the polymer. These properties allow for providing a composition with excellent thermal conductivity.

The present silicone polymers may be used in a variety of applications including, but not limited to, personal care, health care, household, paints, automotive, coatings, laundry detergent, textile treatment, oil and gas, fuel cell, construction product, aerospace product, medical product, electronic application, agriculture, membranes, adhesives, sealants, injection moldable and compression moldable rubbers and plastics, and various silicone based rubbers.

The polymers are suitable for use in personal care applications such as, but not limited to, cosmetics, sunscreen, hair products such as shampoo or conditioner, lotions, creams, etc. Examples of personal care products include, but are not limited to, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications Personal care compositions can include various ingredients such as a carrier, pigment, film formers, emulsifiers, vitamins, plasticizers, surfactants, antioxidants, waxes, oils, solvents, etc.

The polymers of the present invention can be incorporated into a carrier, such as a volatile carrier which quickly volatilizes after application. The volatile carriers can be selected from volatile hydrocarbons, volatile silicones, and mixtures thereof.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

The bulk thermal conductivity (T/C) is determined, unless mentioned otherwise in the examples, by transient method using Hot Disk TPS 500 S instrument. Number-average molecular weight ($M_n$) and poly dispersity index (PDI), with reference to monodisperse polystyrene standards, were determined using Agilent 1260 Infinity gel permeation chromatography system equipped with solvent degasser, Agilent Mixed-BLS (10 um) column, ELSD and RID detector. Melting points were determined by Differential Scanning Calorimetry (DSC) on a TA Instrument (Q 1000) at a heating rate of 10° C. min$^{-1}$ under a nitrogen atmosphere.

Example 1: Diphenyl Sulfone Functionalized Polyorganosiloxane Bearing Terminal Allyloxy Ether Group A three-necked flask was charged with 10 g of 4,4'-Diallyloxy diphenylsulfone, Toluene (50 mL) and platinum catalyst (10 ppm). The resulting mixture was heated to 90° C. while stirring under nitrogen atmosphere and adding 12.7 g of polydimethylsiloxane having terminal dimethylhydrogensiloxy units and consisting of approximately 10 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as waxy solid (GPC: $M_n$=2200 g/mol; PDI=1.3). The polymer has a T/C of 0.195 W/m·K. and peak melting point of 79.5° C.

Examples 2: Diphenyl Sulfone Functionalized Polyorganosiloxane Bearing Terminal Allyloxy Ether Group A three-necked flask was charged with 10 g of 4,4'-Diallyloxy diphenylsulfone, Toluene (50 mL) and platinum catalyst (10 ppm). The resulting mixture was heated to 90° C. while stirring under nitrogen atmosphere and 18 g of polydimethylsiloxane having terminal trimethyl units and consisting of approximately 20 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as waxy solid (GPC: $M_n$=3000 g/mol; PDI=1.4) which has peak melting point of 57° C.

Example 3: Biphenyl Functionalized Polyorganosiloxane Bearing Terminal Methyl Group A three-necked flask was charged with 55.2 g of 4-(allyloxy)-1,1'-biphenyl, toluene (90 mL) and platinum catalyst (15 ppm). The resulting mixture was heated to 72° C. while stirring under nitrogen atmosphere and adding 30 g of polydimethylsiloxane having terminal trimethylsiloxy units, approximately 23 methylhydrogensiloxy units and consisting of approximately 16 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as white solid (GPC: $M_n$=6400 g/mol; PDI=1.9). The polymer had a T/C of 0.194 W/m·K and peak melting point of 55.1° C.

Example 4: Biphenyl Functionalized Polyorganosiloxane Bearing Terminal Biphenyl Ether Group A three-necked flask was charged with 26.8 g of 4-(allyloxy)-1,1'-biphenyl, toluene (90 mL) and platinum catalyst (15 ppm). The resulting mixture was heated to 72° C. while stirring under nitrogen atmosphere and adding 50 g of polydimethylsiloxane having terminal dimethylhydrogensiloxy units, approximately 8 methylhydrogensiloxy units and consisting of approximately 48 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as gummy material (GPC: $M_n$=4500 g/mol; PDI=2.0). The polymer had a T/C of 0.192 W/m·K and peak melting point of 24.7° C.

Example 5: Biphenyl Functionalized Polyorganosiloxane Bearing Q Structure

A three-necked flask was charged with 35.5 g of 4-(allyloxy)-1,1'-biphenyl, toluene (90 mL) and platinum catalyst (15 ppm). The resulting mixture was heated to 72° C. while stirring under nitrogen atmosphere and adding 15 g of polydimethylsiloxane having approximately 4 Q units and approximately 8 units of dimethylhydrogensiloxy. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane resin as white solid (GPC: $M_n$=1800 g/mol; PDI=1.0). The polymer had a T/C of 0.212 W/m·K and peak melting point of 78.4° C.

Example 6: Biphenyl Functionalized Organosiloxane Bearing T Structure

A three-necked flask was charged with 39.4 g of 4-(allyloxy)-1,1'-biphenyl, toluene (90 mL) and platinum catalyst (15 ppm). The resulting mixture was heated to 72° C. while stirring under nitrogen atmosphere and adding 20 g of 3-((dimethylsilyl)oxy)-1,1,5,5-tetramethyl-3-phenyltrisiloxane. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane resin as white waxy solid (GPC: $M_n$=800 g/mol; PDI=1.0). The polymer had a T/C of 0.181 W/m·K and peak melting point of 29.3° C.

Example 7: Polyorganosiloxane Bearing Terminal Biphenyl Ether Group

A three-necked flask was charged with 26.8 g of 4-(allyloxy)-1,1'-biphenyl, toluene (90 mL) and platinum catalyst (30 ppm). The resulting mixture was heated to 72° C. while stirring under nitrogen atmosphere and adding 20 g of polydimethylsiloxane having terminal dimethylhydrogensiloxy units and consisting of approximately 11 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as a soft waxy fluid (GPC: $M_n$=1000 g/mol; PDI=1.0) which has peak melting point of 25.1° C.

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

What is claimed is:

1. A silicone polymer of the Formula (I):

$$M^1{}_a M^2{}_b M^3{}_c D^1{}_d D^2{}_e D^3{}_f T^1{}_g T^2{}_h T^3{}_i Q_j$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C60 alkyl, a C1-C60 alkoxy, or $R^{19}$-A-$R^{20}$—, with the proviso that at least one of $R^4$, $R^{12}$, or $R^{17}$ is $R^{19}$-A-$R^{20}$—, where $R^{19}$ is chosen from a (i) a C1-C60 alkyl or allyl or aryl or vinyl, optionally containing heteroatom(s), (ii) acrylate, or (iii) methacrylate; $R^{20}$ is a divalent organic group selected from a C2-C10 bivalent alkyl group, —O—$(CH_2)_m$—, or —O—C(O)—$(CH2)_m$—, and m is 2-10; and where A is independently selected from:

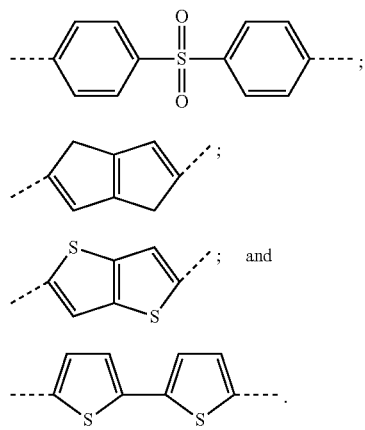

$R^7$, $R^{14}$, $R^{18}$ are independently selected from hydrogen or $OR^{22}$ or unsaturated monovalent radicals or radicals containing a heteroatom selected from oxygen, nitrogen, sulfur, or radicals containing organosilane groups; and the subscripts a, b, c, d, e, f, g, h, i, j are zero or positive subject to the following limitations: 2≤a+b+c+d+e+f+g+h+i+j≤1000, b+e+h>0 and c+f+i≥0, j is 0, and the polymer includes at least one $M^1$, $M^2$, or $M^3$ unit.

2. The polymer of claim 1, wherein $R^{19}$ is chosen from $CH_2=CH_2-(CH_2)_l-$, $CH_2=CH_2-(CH_2)_l-O-$ where l is 0-10.

3. The polymer of claim 1, wherein $R^1$, $R^2$, $R^3$, $R^5$, $R^6$, $R^8$, $R^9$, $R^{10}$, $R^{11}$, $R^{13}$, $R^{15}$, $R^{16}$ are methyl.

4. The polymer of claim 1, wherein the unsaturated monovalent radical is selected from the group of the formulae (I) to (V)

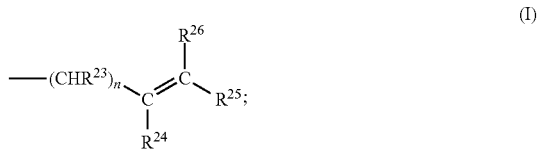

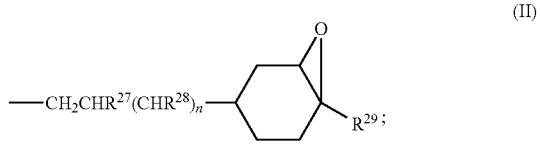

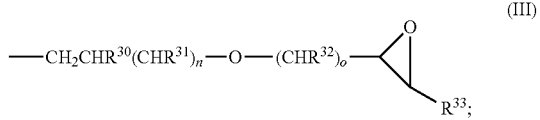

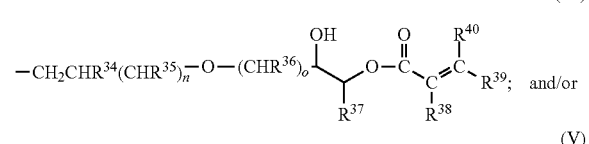

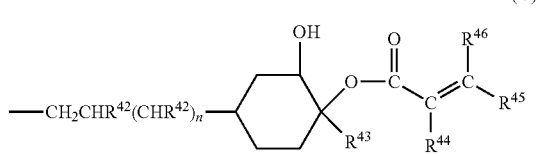

wherein $R^{23}$, $R^{28}$, $R^{31}$, $R^{32}$, $R^{35}$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, $R^{39}$, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6.

5. The polymer of claim 1 wherein the polymer has peak melting temperature of more than 20° C.

6. The polymer of claim 1 wherein the polymer has peak melting temperature is from 23° C. to 100° C.

7. The polymer of claim 1 having a number average molecular weight of from about 100 g/mol to about 12000 g/mol.

8. The polymer of claim 1, where the polymer has a thermal conductivity in the range of 0.1 to 0.5 W/m·K.

9. A product comprising the polymer of claim 1 selected from an automotive product, household product, paint, coating, laundry detergent, textile treatment, oil or gas product, fuel cell, electronic product, agriculture product, aerospace product, medical or health care product, membrane, construction product, adhesive, sealant, injection moldable and compression moldable rubber or plastic, or silicone based rubber.

10. The product of claim 9, wherein the product is selected from a light emitting device, a computer device, a stacked die, a mobile phone, tablets, flip chip package, hybrid memory cube, a touch screen, Wi-Fi device, an automotive technology hifi system, a through-silicon via device, an audio system, a joint between heat pipes and water tanks in solar heated heating, a fuel cell, a wind turbine, a computer chip, a gaming console, a data transfer device, a light device, a battery, a housing, a cooler, a heat exchanging device, a wire, a cable, a heating wire, a refrigerator, a dishwasher, an air conditioning, an accumulator, a transformer, a laser, clothing, a car seat, a medical device, a fire protection, electric motor, a plane, a train, a filament for 3D printing material, a drug delivery system, a transdermal patch, a wound healing patch, a wound dressing patch, a patch for scar reduction, a transdermal iontophoresis, a scaffold for tissue engineering, an anti-microbial device, a wound management device, an ophthalmic device, bioinsert, a prostheses, a body implant, a paint, a structural coating, a masonry coating, a marine coating, a seed coating, a super-spreader, or a controlled release fertilizer.

11. A personal care product comprising the polymer of claim 1.

12. The personal care product of claim 11 in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a skin pad, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouthwash, a massage oil, a toothpaste, a clear gel or stick, an ointment base, a topical wound-healing product, an aerosol talc, a barrier spray, a vitamin and anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

\* \* \* \* \*